United States Patent
Yagita

(12) 
(10) Patent No.: US 6,238,660 B1
(45) Date of Patent: *May 29, 2001

(54) INTERLEUKIN-12 INDUCER AND MEDICAL COMPOSITION

(76) Inventor: Akikuni Yagita, 1-21, Osawa 1-chome, Mitaka-shi, Tokyo 181 (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/967,821

(22) Filed: Nov. 12, 1997

(30) Foreign Application Priority Data

Nov. 11, 1996 (JP) .................................................. 8-315498

(51) Int. Cl.⁷ ........................... A61K 35/60; A61K 35/74
(52) U.S. Cl. ..................................... 424/93.44; 424/244.1; 424/93.44; 424/93.5; 424/274.1; 424/548; 435/254.1; 435/253.4; 514/54; 514/777; 514/59; 514/60
(58) Field of Search ............................... 514/54, 777, 59, 514/60; 424/244.1, 93.44, 93.5, 274.1, 548, 115; 435/254.1, 253.4

(56) References Cited

U.S. PATENT DOCUMENTS

| | | | |
|---|---|---|---|
| 2,972,567 | * | 2/1961 | Novak et al. ........................ 435/103 |
| 3,676,548 | * | 7/1972 | Ose ......................................... 424/92 |
| 4,207,312 | * | 6/1980 | Fujii et al. ............................ 424/180 |
| 4,242,326 | * | 12/1980 | Sugawara et al. .................... 424/116 |
| 4,350,682 | * | 9/1982 | Balassa ................................... 424/64 |
| 5,032,401 | * | 7/1991 | Jamas et al. .......................... 424/426 |
| 5,075,112 | * | 12/1991 | Lane ..................................... 424/434 |
| 5,484,776 | * | 1/1996 | Racz et al. ............................. 514/54 |
| 5,641,761 | * | 6/1997 | Takahashi et al. ..................... 514/54 |

OTHER PUBLICATIONS

Kosuna, New Food Industry 35(2):46–48, 1993.*
Lees et al, Vaccine 12(13): 1160–1166 (1994).*
M. Ghoneum et al: "Immunomodulatory and anticancer effects of active hemicellulose compound (AHCC)" Int. J. Immunotherapy, vol. 11, No. 1, 1995, pp. 23–28 XP002055476.
M. Ghoneum: "NK–Immunomodulation by active hemicellulose compound in 12 cancer patients" Natural Immunity, vol. 13, No. 4, 1994, p. 228 XP002055477.
M. Ghoneum et al: "active hemicellulose compound enhance NK cell activity of aged mice in vivo" Fed Am. Soc. Exp. Biol., vol. 6, No. 4, 1992, p. A 1213 XP002055478.

* cited by examiner

*Primary Examiner*—Francisco Prats
(74) *Attorney, Agent, or Firm*—Sughrue, Mion, Zinn, Macpeak & Seas, PLLC

(57) ABSTRACT

A pharmaceutical composition comprising activated hemicellulose (AHCC), a method for inducing IL-12 in a living body having tumor cells by administering the composition, and a method for treating cancer by administering the composition are provided.

4 Claims, No Drawings

INTERLEUKIN-12 INDUCER AND MEDICAL COMPOSITION

BACKGROUND OF THE INVENTION

1. Field of the Invention

The present invention relates to a substance that can induce interleukin-12 in vivo, and to a medical composition containing the same.

2. Description of the Related Art

Interleukin-12 (IL-12) was originally found as one of cytokinins that can activate NK cells. Subsequent studies revealed that it also promoted growth of and activated T cells that had cytotoxicity specific to tumor cells (Killer T cells), and further it promoted the production of interferon γ (IFN γ) that stimulated activation of killer T cells. Thus IL-12 has attracted attention as a substance effective in treating human cancer patients.

Recently, large-scale production of IL-12 by using a gene manipulation technique was realized in the U.S. (Recombinant IL-12 (rt-IL-12)). Following that, in order to directly deliver IL-12 to cancer cells, a method for directly introducing the IL-12 producing gene into tumor cells, by using gene introduction techniques, has been investigated.

However, sensitivity of rt-IL-12 used in the method is low and administration of a large-amount is needed, for example, to treat human cancer. Such large-amount dosage causes various side effects including fever and inappetence. Besides these serious side effects, several problems regarding this method are pointed out, that is, the gene manipulation procedure is so complicated that it is labor intensive and lacks economical feasibility.

For using IL-12 to prevent tumor growth or cause regression, there are two methods; one is to externally administrate IL-12, and the other is to induce in vivo production of IL-12. Such induced IL-12 does not raise abnormal immune response, thereby resolving intrinsic problems of rt-IL-12. At the same time, such IL-12 is highly effective, thus extensive tumor loss regression effect can be expected. However, before the instant invention an effective substance that could induce IL-12 of its own in vivo had not been found.

SUMMARY OF THE INVENTION

In view of the above circumstances, it is an object of the present invention to provide a method for inducing IL-12 in vivo in a tumor bearing patient and a substance having such an induction effect, and further to provide a medical composition obtained by utilizing the same.

According to the present invention, there is provided an interleukin-12 inducer containing activated hemicellulose (AHCC) and a medical composition containing the same.

DETAILED DESCRIPTION OF THE INVENTION

Hereunder, the detailed description is made of the present invention.

Activated HemiCellulose Compound (AHCC) of the present invention is a known compound as a biologically active substance which is obtained by enzyme treatment of plant fiber existing in the cell wall of fungal mycelia. Preferable AHCCs for use in the present invention are selected from (1) β-D-glucan, (2) α-D-glucan, and (3) a mixture of β-D-glucan and α-D-glucan. AHCC contains in addition to heteroglucan such as β-(1-3)D-glucan, β-(1-6) D-glucan and α-(1-4)D-glucan; peptidoglycan, proteoglucan, lectin, nucleic acid and indigestive polysaccharide. Dojin News, No. 34, pages 2–4 (1985); the entire content of which is hereby incorporated by reference.

However, it had not been previously known that AHCC could induce IL-12, until the fact was newly found by the present inventor.

The IL-12 inducer of the present invention may consist only of the above described AHCC, but preferably further contains components of fungal mycelium (*Eubasidomycetes*). Examples of such components of mushroom's mycelium include PSK that is a component of a polypore's mycelium (Polyporacede) and used as a known anti-cancer agent, SPG that is a component of *Schizophyllum commune mycelium's mycelium,* and lentinan that is a component of a shiitake's mycelium (*Lentinula edodes*), but are not limited thereto.

Further, such components of fungal mycelium include, for example, that of agaricus, *Ganoderma lucidum,* ningyotake, kawariharatake, niousimeji, kabenoanatake, *Griforia frondosa, Hericium erinaceum,* an oyster fungal (*Pleurotus ostreatus*), mannnenntake (*Ganoderma lucidum*), *Panellus serotinus,* kobutake, *Lenzites betulina,* a matsu-take (*Tricholoma matsutake*), bekkoutake, nametake and *Frammulina velutipes.*

The IL-12 inducer of the present invention may be composed of only above described AHCC and components of fungal mycelium, but preferably contains bacterial components of hemolytic streptococci in addition to the above. Examples of such bacterial components of hemolytic streptococci include, OK-432 that is a known anti-cancer agent, but are not limited thereto.

These are known substances as biological response modifiers (BRMs).

It has been revealed that in progressed cancer or end-stage cancer, tumor regression or disappearance could not be obtained by established conventional treatments of modern medicine such as surgery, administration of an anti-cancer agent, radiotherapy and hormonotherapy. On the other hand, the IL-12 inducer of the present invention is effective for tumor regression and disappearance in progressed or end-stage cancer. Effectiveness can be determined by, for example, assay of body fluid or parts, NMR, surgery or palpitation. This fact was newly discovered by the present inventor. This is the first unique effect of the present invention.

No side effects were found in the administration of the IL-12 inducer of the present invention. Rt-IL-12 produced by the conventional gene manipulation method has low sensitivity and therefore requires administration in a large volume, which often induces various side effects and exerts upon patients serious damage. On the other hand, the reason why there is no concern for side effects, is because the IL-12 inducer of the present invention can activate the IL-12 production ability naturally existing in a living body as its basic action mechanisms, it is not necessary to externally administer a substance causing side effects.

This fact is newly found by the present inventor and is the second unique effect of the present invention.

The medical composition of the present invention contains the above described IL-12 inducer as the main component. The medical composition of the present invention can be used, for example, as an anti-cancer agent but not limited thereto.

The formulation of the medical composition of the present invention to be administered to a human or animal is not specifically limited. The medical composition of the present invention may be, for example, retained on carriers and suitably prepared into various formulations commonly used in medicine.

As such carriers, at least one selected from solid, semi-solid or liquid diluent, filler and other support for formulation may be used at a ratio of for example, 0.1% to 99.5%, preferably 0.5% to 90%. The medical composition of the present invention may be safely administered perorally or parenterally. The route of parenteral administration includes local administration such as intratissue administration, subcutaneous administration, intramuscular administration, intra arterial/intravenous administration and per rectum administration. Formulations suitable for the above administration routes may be prepared using known practical means.

For example, when used as an anti-cancer agent, the dosage is preferably determined according to age, body weight, administration route used, type of disease and severity. In the case of administration for human patients, it is, for example, generally administered perorally at a dosage of 100 to 20,000 mg/day as the active compound, preferably 1,000 to 10,000 mg/day as the active compound. For parenteral administration, the dosage largely differs according to the administration route, but in general, 100 to 1,000 mg/day, preferably 200 to 500 mg/day may be used. According to each case, a lower dosage may be enough, or a larger dosage may be required. Dosage can be divided into two to four doses per day. Depending on the patient and specific constituents of the anticancer formulation, the effective dose range may vary. Tumor stasis or regression or other clinical indicators can be used to determine an appropriate dose.

For peroral administration, solid or liquid formulation may be used such as pulvis, powder, granule, tablet, capsule, syrup, elixir and suspension.

Pulvis is prepared by pulverizing the active substance to suitable fineness. Powder is prepared by pulverizing the active substance to suitable fineness, and then mixing it with medical carrier prepared to the same fineness, for example, dietary carbohydrate such as starch and mannitol, and other vehicles. If necessary, a corrective, preservatives, dispersing agent, tinction, aromatic and others may be added therein.

Capsule is prepared by filling the above described pulverized pulvis, powder or granulated tablets into an outer capsule, for example, a gelatin capsule. Before filling, lubricant or drifting agent, for example, colloidal silica, talc, magnesium stearate, calcium stearate and solid polyethylene glycol may be arbitrarily mixed therein. Efficacy of medicine in capsule formulation after intake is improved by adding therein a disintegrator or solubilizing agent such as carboxymethyl cellulose, calcium carboxymethyl cellulose, low-substituted hydroxypropyl cellulose, sodium crosskarumelose, sodium carboxystarch, calcium carbonate and sodium carbonate.

Soft capsule may be prepared by suspending fine powders of the present product in plant oil, polyethylene glycol, glycerin, and a surfactant and encapsulate them within gelatin sheet.

Granules may be prepared by mixing the pulverized active substance and above described vehicle, a disintegrator and, if necessary, binder (for example, sodium carboxymethyl cellulose, hydroxypropyl cellulose, methyl cellulose, hydroxypropylmethyl cellulose, gelatin, polyvinylpyrrolidone, polyvinylalchol, and the like), humectant (for example, syrup, starch, gum arabic, cellulose solution, macromolecule solution, and the like), kneading them, and letting them pass through a sieve. Alternative to granulate powders, granule may be obtained by pulverizing slug of insufficient shapes which had raised at tableting. Dissolution delaying agent (for example, paraffin, wax, hardened castor oil, and the like), a reabsorption agent (for example, quaternary salts or the like) or adsorbent (for example, bentonite, Kaolin, dicalcium phosphate, and the like) may be mixed therewith in advance.

Tablets may be prepared by adding lubricant including stearic acid, stearate, talc, mineral oil, and the like to thus obtained granules and then tableting. Thus obtained intact tablets may be covered with film coating or sugar coating.

The mixing process of the active substance of the present invention and fluid inactive carrier may be immediately followed by the tableting process without above described granulation process or slug process. Coatings that can be used include transparent or semi-transparent protect coating of closed coating of shellac, coating of sugar or macromolecules and finish coating consisting of wax.

Other peroral formulation, including syrup, elixir and suspension can be prepared in dosage per unit so that a predetermined amount of the medical substance is contained in a predetermined amount of each formulation. Syrup may be prepared by dissolving the active agent in a suitable flavored water solution. Elixir may be prepared by using non-toxic alcoholic carrier. Suspension may be prepared by dispersing the active substance in non-toxic carriers. A suspending agent or emulsifier (for example, ethoxylated isostearyl alcohols and polyoxyethylene sorbitol esters), preservative, corrective (for example, peppermint oil and saccharin) and other agents may be arbitrarily added thereto.

If necessary, the dosage unit for peroral administration may be contained in microcapsules. In this method, the active substance is coated or buried in macromoleculars or wax, thereby prolonging action time or delaying the release.

Subcutaneous, intramuscular, intra-arterial and intravenous administration can be given by using liquid dosage unit formulation, for example injection consisting of solution or suspension. These formulation is prepared by dissolving or suspending a predetermined amount of the active substance in non-toxic liquid carrier suitable for objective injection route including aqueous or oleaginous solvent and then sterilizing the solution or suspension. Alternatively, a predetermined amount of the powder or freeze-dried active substance may be placed in a vial and the vial and contents thereof may be sterilized and sealed. In this case, the active substance is to be dissolved or mixed immediately before the administration, and spare vials or carriers can be reserved. Non-toxic salts or salt solution to prepare an isotonic injection may be added and further a stabilizer, preservative, suspending agent emulsifier and others may be combinedly used.

The formulation for per rectal administration may be prepared by mixing the active substance with hydrophobic or hydrophilic suppository base including, for example, polyethylene glycol, cacao butter, higher esters (for example, myristyl ester of palmitic acid) and mixture thereof.

AHCC, components of fungal mycelium, and bacterial components of hemolytic streptococci of the present invention have the effect of inducing IL-12. Accordingly, a method of inducing IL-12 in vivo by administering these substances is within the scope of the present invention.

Further, AHCC, components of fungal mycelium, and bacterial components of hemolytic streptococci of the present invention have the effect to induce IL-12.

Accordingly, a method to cure cancer by administering them in single or multiple administration at a dose that can induce IL-12 is within the scope of the present invention.

EXAMPLES

The present invention may be better illustrated with reference to the following examples. However, the present invention is not limited thereto.

Example 1

Example of Single Administration of AHCC

A human patient suffering from esophagus cancer (72-year-old, male) showing infiltration at cervical lymph nodes and intraperitoneal lymph nodes, no indication for surgery, unresponsive to radiotherapy, unable to perform oral intake of other than water.

To this patient, AHCC was continuously administered at a dosage of 3.0 g/day. One month after the start of the administration, the patient became able to eat 30% gruel or 50% gruel. The level of serum SCC tumor marker was 23 ng/mL before the administration (normal level: 2.0 ng/mL), but improved to 1.3 ng/mL one month after. By further continuing the administration, he became able to eat 100% gruel three months after the administration commencement, when the tumor was confirmed to have completely disappeared by fluoroscopic and CT examinations of esophagus.

After a three-month administration of AHCC, serum NK activity was as high as 68% (normal value: lower than 40%), and serum IL-12 level was also as high as 78 pg/mL (normal value: lower than 7.2 pg/mL). These result are listed in Table 1.

In Table 1, CD4 represents helper T cells, and CD8 represents killer T cells. The CD4/CD8 ratio represents degree of increase in killer T cells, and a value less than 1 represents increase in killer T cells. The range of normal values is 1.0 to 1.5. The CD4/CD8 ratio in Example 1 was 0.75, showing that cytotoxic killer T cells was increased.

Example 2

Example of Single Administration of AHCC

In a human patient suffering from orchioncus (36-year-old, male), primary cancer in the right testis was excised. After the surgery, metastasis of an infant's head size to a peritoneal lymph node occurred. AHCC at a dosage of 3.0 g/day was continuously administered orally to this patient. After one month, the size of tumor decreased approximately by half, and after three months, the tumor completely disappeared.

After three months administration, NK activity was low at 13%, but IL-12 level was extremely high at 120 pg/mL. It was suggested that the anti-tumor effect of AHCC was not through NK activity. These results were listed in Table 1.

TABLE 1

| Human patient | Symptoms | NK Activity | Serum IL-12 level | Treatment evaluation | CD4/CD8 ratio |
|---|---|---|---|---|---|
| Example 1 | 72-year-old; male | esophagus cancer; surgery impossible; radiotherapy unresponsible; end-stage | 68% | 78 pg/mL | CR; complete regression | 0.75 |

TABLE 1-continued

| Human patient | Symptoms | NK Activity | Serum IL-12 level | Treatment evaluation | CD4/CD8 ratio |
|---|---|---|---|---|---|
| Example 2 | 36-year-old; male | cancer right testis tumor; infant's head size metastasis to retroperitoneal lymph node; end-stage cancer | 13% | 120 pg/mL | CR complete regression | 0.52 |

Examples 3 to 6

Examples of Combined Administration of AHCC with Shark Cartilage

To the human cancer patients listed in Table 2, AHCC at a dosage of 3.0 g/day and concomitantly shark cartilage (β shark) at 20 g/day were continuously administered orally. After three months administration, treatment evaluation and NK Activity, IL-12 level and CD4/CD8 ratio were evaluated. According to Examples 3 and 6, tumor regression of 50% or more was obtained in either case. However, the NK activity in either example was within the normal range, indicating that the NK activity was not elevated. In either of Examples 3 to 6, the IL-12 level was high significantly exceeding the normal range. It was suggested that IL-12 was involved in tumor regression. Further, from the results of previous immunological investigations, it has been shown that concomitant use of shark cartilage had no effect on the NK activity and did not elevate the IL-12 level.

TABLE 2

| Human patient | Symptoms | NK activity | Serum IL-12 level | Treatment evaluation | CD4/CD8 ratio |
|---|---|---|---|---|---|
| Example 3 | 72-year-old; male | stomach cancer; progressed stage | 24% | 240 ng/mL | CR complete regression | 0.34 |
| Example 4 | 57-year-old; male | caecum cancer; carcinomatous peritonitis; end-stage cancer | 62% | 230 pg/mL | CR complete regression | 0.42 |
| Example 5 | 69-year-old; male | stomach cancer; metastasis to liver; end-stage cancer | 62% | 103 pg/mL | CR complete regression | 0.62 |
| Example 6 | 71-year-old; female | hepatic cancer; metastasis to lung; end-stage cancer | 68% | 78 pg/mL | PR; metastasis disappear | |

Examples 7 and 8

Examples of Combined Administration of AHCC, PSK and Shark Cartilage

To the human cancer patients listed in Table 3, first, continuous oral administration of AHCC at a dosage of 3.0 to 6.0 g/day combined with shark cartilage at a dosage of 20 g/day. Until three months, tumor regression was not found and the IL-12 level was not elevated.

Then, to the human cancer patients listed in Table 3, in addition to the continuous oral administration of AHCC at a dosage of 3.0 to 6.0 g/day combined with shark cartilage at a dosage of 20 g/day, PSK (Sankyo Co. Ltd., Krestin) at 3.0 g/day was further combinedly administered. After addition of PSK administration, the IL-12 level was elevated and at the same time, partial regression (PR) effect of 50% or higher for tumor was obtained.

It was shown that concomitant use of shark cartilage had no effect on the NK activity and did not elevate the IL-12 level. Further, since single administration of PSK at 3.0 g/day had not shown a regression effect for lung tumor, the observed regression effect was thought to be achieved by the concomitant use of AHCC and PSK. It was suggested that PSK also promoted the IL-12 production.

TABLE 3

| | Human patient | Symptoms | NK activity | Serum IL-12 level | Treatment evaluation | CD4/ CD8 ratio |
|---|---|---|---|---|---|---|
| Example 7 | 67-year-old; male | left lung cancer; metastasis to right lung; liver; end-stage cancer | 32% | 240 pg/mL | PR; right lung metastasis disappear | 0.43 |
| Example 8 | 73-year-old; female | right lung cancer; metastasis to left lung; metastasis to liver; end-stage cancer | 29% | 340 pg/mL | PR; lung metastasis disappear | 0.43 |

Comparative Examples 1 and 2

Examples of Concomitant Use of OK-432, PSK and SPG (or Lentinan)

As shown in Table 4, the effect of multiple immunotherapy was tested in Comparative example 1, by subcutaneous administration of OK-432 (Chugai Pharmaceutical Co. Ltd., Picibanil) at a dosage of 5 KE/W, oral administration of PSK (Sankyo Co. Ltd., Krestin) at 3.0 g/day and further intramuscular injection of SPG (Kaken Pharmaceutical Co. Ltd., Sonifilan) at vial/W. In Comparative Example 2, the effect of multiple immunotherapy was also tested in the same manner as in Comparative Example 1, except that in stead of SPG, Lentinan (Yamanouchi Pharmaceutical Co. Ltd., Lentinan) was intravenously injected at 400 mg/w.

In either example, dramatic tumor regression was achieved. Further, the IL-12 level was high in either example. It was suggested that the anti-cancer effect obtained by the multiple immunotherapy may be due to the increased production of IL-12.

TABLE 4

| | Human patient | Symptoms | NK activity | Serum IL-12 level | Treatment evaluation | CD4/ CD8 ratio |
|---|---|---|---|---|---|---|
| Comparative example 1 | 23-year-old; male | stomach cancer; carcinomatous peritonitis; end-stage cancer | 32% | 240 pg/mL | CR complete regression | 0.72 |
| Comparative example 2 | 72-year-old; male | hepatic cancer; carcinomatous peritonitis; end-stage cancer | 40% | 260 pg/mL | PR 3/4 of hepatic cancer disappearance | 0.32 |

For patients with progressed cancer or end-stage cancer, example in which tumor regression or disappearance was achieved by administering BRM preparation to induce the IL-12 production has not been previously reported. This was newly found by the present inventor. It was clarified that the observed effect was not only mediated by the NK activity but also by the induction of IL-12 and an increase of killer T cells. It was also found that when anti-cancer effect is to be enforced by induction of IL-12, concomitant administration of shark cartilage that inhibits neovascularization was also effective.

Furthermore, it was found that additional PSK administration was effective to promote anti-cancer effect of AHCC. This promotion effect was especially remarkable in lung cancer, hepatic cancer, stomach cancer, large intestine cancer, pancreatic carcinoma and kidney cancer.

It was found that IL-12 could be induced by concomitant administration of BRM preparations other than IL-12 or by concomitant administration of three drugs of OK-432, PSK and SPG (or Lentinan).

At present circumstances, even by making the most use of treatments in the modern medicine, including surgery, administration of anti-cancer agent, radiotherapy and hormonotherapy, few effect can be expected in the treatment of progressed cancer or end-stage cancer. Administration of an IL-12 inducer of the present invention or a medical composition containing the same as the major component is highly effective in the practical use, showing high efficacy in the treatment of the progressed cancer or end-stage cancer or in the improvement of QOL.

What is claimed is:

1. A pharmaceutical composition comprising AHCC as an active ingredient in an amount effective to induce interleukin-12 in combination with at least one of shark cartilage and components of hemolytic streptococci, and a pharmaceutically acceptable carrier.

2. The pharmaceutical composition as claimed in claim 1, which further contains in addition to the AHCC, components of fungal mycelium other than AHCC.

3. The pharmaceutical composition as claimed in claim 1, which contains components of hemolytic streptococci.

4. The pharmaceutical composition according to claim 1, comprising shark cartilage.

* * * * *

UNITED STATES PATENT AND TRADEMARK OFFICE
Certificate

Patent No. 6,238,660 B2                                                    Patented: July 3, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Craig A. Rosen, Laytonsville, MD (US); William A. Haseltine, Washington, DC (US); and Steven M. Ruben, Brookeville, MD (US).

Signed and Sealed this Nineteenth Day of April 2011.

MANJUNATH RAO
*Supervisory Patent Examiner*
Art Unit 1656
Technology Center 1600

UNITED STATES PATENT AND TRADEMARK OFFICE
CERTIFICATE OF CORRECTION

PATENT NO.         : 6,238,660 B1                                       Page 1 of 1
APPLICATION NO.    : 08/967821
DATED              : May 29, 2001
INVENTOR(S)        : Akikuni Yagita It is certified that error appears in the above-identified patent and that said Letters Patent is hereby corrected as shown below:

This certificate supersedes the Certificate of Correction for inventorship issued April 19, 2011.
The certificate is vacated since correction of inventorship was not requested for this patent.

The correct inventorship of this patent is: --Akikuni Yagita, Tokyo (JP)--.

Signed and Sealed this
Sixth Day of December, 2011

David J. Kappos
*Director of the United States Patent and Trademark Office*